(12) United States Patent
Zhang et al.

(10) Patent No.: US 11,617,867 B2
(45) Date of Patent: Apr. 4, 2023

(54) DRUG-COATED BALLOON CATHETER

(71) Applicant: Hangzhou Weiqiang Medical Technology Co., Ltd., Hangzhou (CN)

(72) Inventors: Tingchao Zhang, Hangzhou (CN); Jing Li, Hangzhou (CN)

(73) Assignee: HANGZHOU ENDONOM MEDTECH CO., LTD., Hangzhou (CN)

( * ) Notice: Subject to any disclaimer, the term of this patent is extended or adjusted under 35 U.S.C. 154(b) by 635 days.

(21) Appl. No.: 16/749,278

(22) Filed: Jan. 22, 2020

(65) Prior Publication Data

US 2020/0155812 A1    May 21, 2020

Related U.S. Application Data

(63) Continuation of application No. PCT/CN2018/097274, filed on Jul. 26, 2018.

(30) Foreign Application Priority Data

Aug. 2, 2017 (CN) .......................... 201710653529.7

(51) Int. Cl.
*A61M 29/00* (2006.01)
*A61M 25/10* (2013.01)
*A61M 25/00* (2006.01)

(52) U.S. Cl.
CPC ......... *A61M 25/10* (2013.01); *A61M 25/0032* (2013.01); *A61M 2025/0004* (2013.01);
(Continued)

(58) Field of Classification Search
CPC ...... A61M 25/1011–2025/1015; A61M 31/00; A61M 25/10; A61M 2025/1081;
(Continued)

(56) References Cited

U.S. PATENT DOCUMENTS 5,505,702 A * 4/1996 Arney ................. A61M 25/104
604/103.1
10,052,462 B2 * 8/2018 Belafsky ............ A61M 25/1011
(Continued)

FOREIGN PATENT DOCUMENTS

CN          103316382 A     9/2013
CN          203989422 U    12/2014
(Continued)

OTHER PUBLICATIONS

The Extended European Search Report issued corresponding EP Application No. EP 18840539.3 dated Apr. 7, 2021.
International Search Report from PCT/CN/2018/097274; dated Nov. 8, 2018.

*Primary Examiner* — Rebecca E Eisenberg
(74) *Attorney, Agent, or Firm* — Fish IP Law, LLP

(57) ABSTRACT

Disclosed is a balloon catheter (1000) with a drug coating. The balloon catheter comprises a pushing catheter (310), at least one expandable first balloon (100) located at a distal end of the pushing catheter (310), and a pre-expansion mechanism. The first balloon (100) is fixedly arranged on the pushing catheter (310). The pre-expansion mechanism (200) comprises an expansion sleeve (220) and a connector (240). The expansion sleeve (220) is used for housing the first balloon (100) before the first balloon (100) is not expanded and when same is pre-expanded. The connector (240) is connected to the expansion sleeve (220) and axially moves with respect to the pushing catheter (310) after the first balloon (100) is pre-expanded, so that the first balloon (100) is exposed outside the expansion sleeve (220). The balloon catheter (1000) with a drug coating can effectively pre-expand a lesion location and can also effectively prevent the loss of a balloon with a drug coating during a delivery process, and is simple in terms of a surgical operation process.

24 Claims, 6 Drawing Sheets

(52) U.S. Cl.
CPC ............... *A61M 2025/1004* (2013.01); *A61M 2025/105* (2013.01); *A61M 2025/1015* (2013.01); *A61M 2025/1061* (2013.01)

(58) Field of Classification Search
CPC ............ A61M 29/02; A61M 2025/105; A61M 2025/1004; A61M 2025/0004
See application file for complete search history.

(56) References Cited

U.S. PATENT DOCUMENTS

| | | | |
|---|---|---|---|
| 2008/0243168 A1* | 10/2008 | Ho | A61M 25/1011 606/194 |
| 2010/0228333 A1* | 9/2010 | Drasler | A61M 25/10 604/103.05 |
| 2012/0211490 A1 | 5/2012 | Wesselmann et al. | |
| 2013/0096604 A1* | 4/2013 | Hanson | A61M 25/104 606/194 |
| 2014/0052105 A1 | 2/2014 | Hattangadi et al. | |
| 2015/0190618 A1 | 7/2015 | Kantor | |

FOREIGN PATENT DOCUMENTS

| | | | | |
|---|---|---|---|---|
| CN | 106420128 A | | 2/2017 | |
| CN | 106994204 A | | 8/2017 | |
| GB | 2209471 A | * | 5/1989 | ........ A61M 16/0488 |
| WO | WO-03103762 A1 | * | 12/2003 | ....... A61B 17/12045 |
| WO | 2016199117 A1 | | 12/2016 | |

\* cited by examiner

DRUG-COATED BALLOON CATHETER

TECHNICAL FIELD

The present disclosure relates to the field of medical device technology, in particular to a drug-coated balloon catheter.

BACKGROUND

Arterial stenosis has always been a type of disease that plagues people. In order to cure such disease, people have undergone treatment stages such as bare-balloon, bare-metal stent (BMS), and drug-eluting stent (DES), but these treatment options have different defects. At present, drug-coated balloon (DCB) catheters emerged. DCB catheters not only establish channels for blood circulation through balloon expansion, but also carry drugs on the balloon that can effectively inhibit the proliferation of smooth muscle cells and prevent blood vessel restenosis.

Before a lesion segment is expanded and treated with a DCB, a normal drug-free balloon must be used to pre-expand the lesion so that the DCB can smoothly enter the lesion and avoid damages to the blood vessel caused by one-time overexpansion. However, pre-expansion requires using an additional normal balloon, which increases the complexity of the surgery, and after pre-expansion, the flushing of the high-speed flowing blood causes a loss of drug volume of the DCB during transmission.

SUMMARY

In view of the afore-mentioned disadvantages in the prior art, the present disclosure provides a DCB catheter that is simple to operate and has a higher usage rate of drugs.

The implementations of the present disclosure provides the following technical solutions to achieve the afore-mentioned purposes:

The present disclosure provides a DCB catheter, including:
  a pushing catheter;
  a first balloon fixedly disposed on the pushing catheter; and
  a pre-expansion mechanism including:
    an expansion cover for accommodating the first balloon before the first balloon is expanded and when the first balloon is being pre-expanded, and
    a connecting member that connects the expansion cover and moves axially with respect to the pushing catheter after the first balloon is pre-expanded so as to expose the first balloon outside the expansion cover.

The present disclosure has at least the following beneficial effects by providing a pre-expansion mechanism on the exterior of the DCB catheter:

(1) The pre-expansion mechanism is transported together with the DCB into the patient's body, and the pre-expansion mechanism realizes pre-expansion of the lesion segment, so that the DCB can smoothly enter the lesion, thereby increasing the area of the inner wall of the blood vessel at the lesion segment that may contact the surface of the DCB, and increasing the amount of medication delivered to the blood vessel wall after the expansion of the DCB, improving the therapeutic effect;

(2) The pre-expansion mechanism is sleeved outside the DCB, and is transported to the lesion segment together with the DCB during use, thereby effectively protecting the DCB from being flushed by blood flow and reducing the drug loss during the transportation process;

(3) No need to use additional pre-expanded balloons, reducing the complexity of surgery and the cost of surgery, and save operation time.

BRIEF DESCRIPTION OF THE DRAWINGS

To illustrate the technical solutions according to the embodiments of the present disclosure or in the prior art more clearly, the accompanying drawings for describing the embodiments or the prior art are introduced briefly in the following. Apparently, the accompanying drawings in the following description are only some embodiments of the present disclosure, and persons of ordinary skill in the art can derive other drawings from the accompanying drawings without creative efforts.

DETAILED DESCRIPTION OF THE EMBODIMENTS

The present disclosure will be described in details in combination with the accompanying drawings and embodiments such that the purpose, technical solution and advantages of the present disclosure will be more apparent. It should be understood that the particular embodiments are described for the purpose of illustrating as opposed to restricting the present disclosure. The descriptions are merely specific embodiments of the present disclosure, but are not intended to limit the protection scope of the present disclosure. Any variation or replacement readily figured out by a person skilled in the art within the technical scope disclosed in the present disclosure shall all fall within the protection scope of the present disclosure.

Firstly, it should be noted that in the field of interventional medicine, the end of a device near the operator is generally referred to as the proximal end (i.e., the operating end), and the end of the device away from the operator is referred to as the distal end (i.e., the insertion end). Specifically, the distal end refers to one end of the device that can be freely inserted into an animal or a human body. The near end refers to one end for user or machine operation or one end for connecting other devices. Moreover, the use of the terms first, second, and the like does not mean any order or importance, but the terms first, second, and the like are used to distinguish one element from another.

The present disclosure provides a DCB catheter that includes a pushing catheter, at least an expandable first balloon disposed on the distal end of the pushing catheter, and a pre-expansion mechanism. At least part of the surface of the first balloon is covered by a drug coating. The pre-expansions mechanism includes an expansion cover that is expandable and movably sleeved outside the first balloon, and a connecting member that is connected with the proximal end of the expansion cover. The connecting member moves axially with respect to the pushing catheter.

Referring together to FIG. 1 to FIG. 9, a DCB catheter 1000 according to a first embodiment of the present disclosure is provided. The DCB catheter 1000 includes a pushing catheter 310, a balloon 100 and a pre-expansion mechanism 200 both disposed on the pushing catheter 310. The pushing catheter 310 has an insertion end (i.e., a distal end) and an operating end (i.e., a proximal end) opposite to each other. The balloon 100 is located at the distal end of the pushing catheter 310. The outer surface of the balloon 100 is at least partially covered by a drug coating 30.

Figure 3:
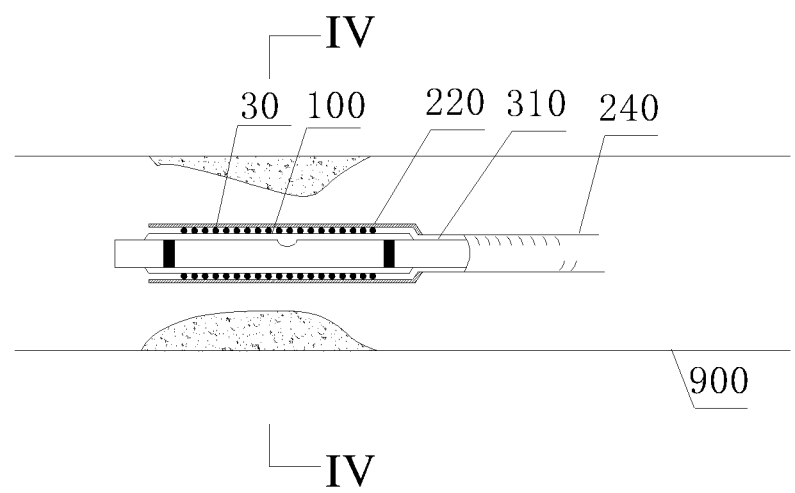
FIG. 3 is a schematic diagram of the DCB catheter of FIG. 1 before the balloon is pre-expanded.
Figure 4:
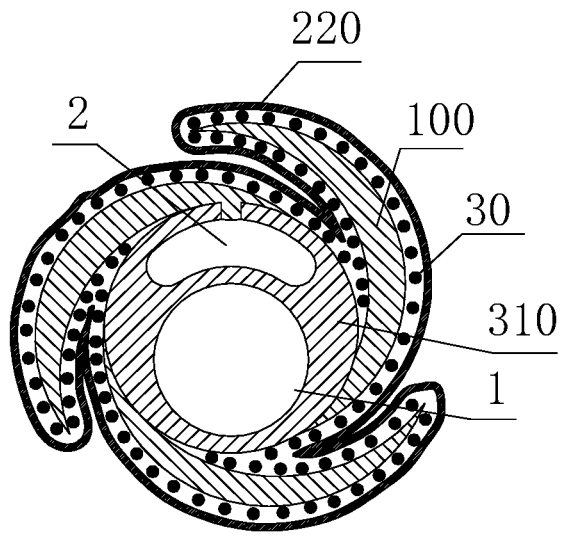
FIG. 4 is a cross-sectional diagram of the DCB catheter of FIG. 3 along the line IV-IV.

As shown in FIG. 3 and FIG. 4, the balloon 100 has a plurality of flaps before being expanded. Alternatively, the balloon 100 has three to six flaps before being expanded. The balloon 100 is fixed to the distal end of the pushing catheter 310. The fixing method is a conventional technique such as welding, bonding or fixing by a fixing member, and details are not described herein again. The balloon 100 is composed of a proximal end portion, a distal end portion, and a working portion between the proximal end portion and the distal end portion. The proximal end portion and the distal end portion of the balloon 100 are substantially conical, and the working portion of the balloon 100 is substantially cylindrical. The working portion is located in the middle of the balloon 100. The working portion has a diameter of about 2-15 mm. The balloon 100 has a length of approximately 30-320 mm. The effective length of the balloon 100 (i.e., the length of the working portion) is approximately 20-300 mm. The diameter, length, effective length, and other standard measurements of the balloon 100 are selected according to the diameter of the diseased blood vessel to be treated. The drug coating 30 is mainly disposed in the working portion of the balloon 100. The drug coating 30 contains an active drug having an action of inhibiting smooth muscle cell proliferation, such as paclitaxel or rapamycin. The drug coating 30 further contains a polyol, an organic acid salt or the like as a carrier. In the present embodiment, paclitaxel is used as an active drug and mannitol is used as a carrier. The coating of the drug coating 30 is prior art and will not be described herein. The working portion of the balloon 100 is cylindrical, so that the filled balloon 100 has good adherence and can be attached to the inner wall of the blood vessel with a certain length, and can effectively deliver the active drug to the blood vessel wall.

Figure 1:
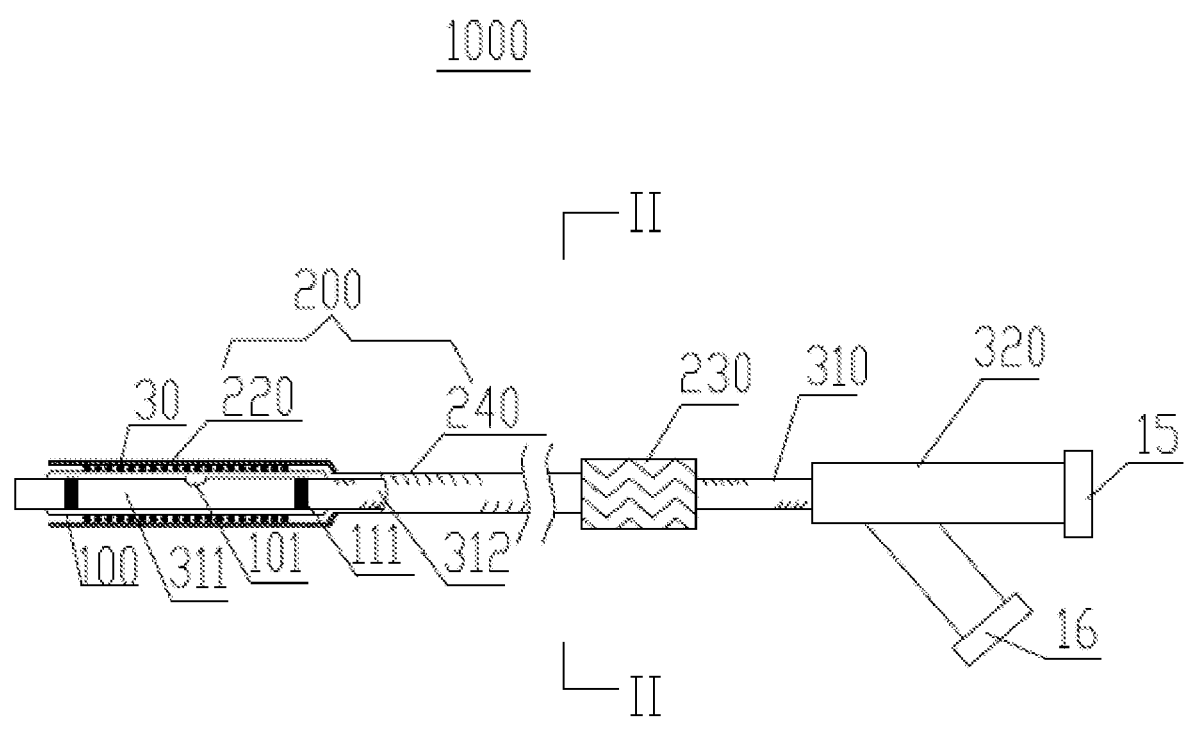
FIG. 1 is a schematic structural diagram of a DCB catheter according to the first embodiment of the present disclosure.
Figure 2:
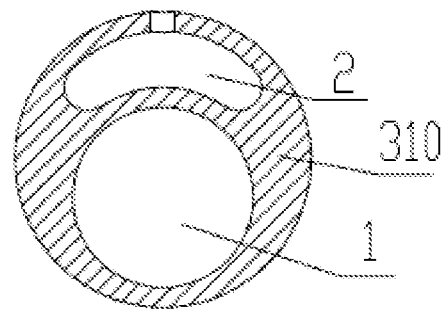
FIG. 2 is a cross-sectional diagram of the pushing catheter of the DCB catheter of FIG. 1 along the line II-II.

As shown in FIG. 1 and FIG. 2, in the present embodiment, the pushing catheter 310 passes axially through both ends of the balloon 100, and is in a sealed connection to the balloon 100. The pushing catheter 310 has a first section 311 accommodated in the balloon 100 and a second section 312 exposed outside the balloon 100. The pushing catheter 310 is provided with a guide wire cavity 1 in the axial direction and a filling cavity 2 that is separated from the guide wire cavity 1. The cavities of the guide wire cavity 1 and the filling cavity 2 are not connected to each other. The guide wire cavity 1 penetrates through the pushing catheter 310 and is in communication with the balloon 100. The guide wire cavity 1 is for accommodating a guide wire (not shown). In one embodiment, the number of filling cavities 2 is one, and the distal end of the filling cavity 2 is in communication with the interior of the balloon 100 for filling and pressure relieving of the balloon 100. It can be understood that in another embodiment, in order to increase the filling and pressure relieving speed of the balloon 100, the number of filling cavities 2 may be multiple, and each filling cavity 2 is in communication with the inner cavity of the balloon 100. As such the amount of fluid flowing into/out of the balloon 100 per unit time is increased, thereby increasing the filling/pressure relieving speed of the balloon 100 and reducing the surgical time.

Referring again to FIG. 1 and FIG. 2, the DCB catheter 1000 also includes a catheter set 320 disposed on the proximal end of the pushing catheter 310. The catheter set 320 is fixed to the proximal end of the pushing catheter 310. The catheter set 320 is provided with a guide wire port 15 in communication with the guide wire cavity 1 and a filling port 16 in communication with the filling cavity 2. The first section 311 of the pushing catheter 310 is provided with a balloon filling port 101. The two ends of the filling cavity 2 are connected to the filling port 16 and the balloon filling port 101, respectively. As such, the filling port 16, the filling cavity 2, and the balloon filling port 101 form a passage for filling and pressure relieving of the balloon 100. The filling port 16 can be connected to an external pressure pump, and the pressurized liquid enters or flows out of the interior of the balloon 100 through the filling port 16, the filling cavity 2, and the balloon filling port 101 to achieve filling expansion or pressure relieving of the balloon 100.

The first section 311 of the pushing catheter 310 is provided with at least one development positioning device 111 to facilitate indicating the position of the balloon 100 by displaying the position of the development positioning device 111 under instrumental detection. The development positioning device 111 is made of a radiopaque material and has a structure such as a ring, a filament, a ribbon, a dot, or a sheet. The development positioning device 111 is optionally in the form of a developing ring. The development positioning device 111 can be set one or more separately. The fixing manner of the development positioning device 111 may be a conventional technique in the technical field such as welding, bonding, hot pressing, and riveting, and will not be described herein.

The pre-expansion mechanism 200 of the DCB catheter 1000 includes an expansion cover 220. The expansion cover 220 is used to accommodate the balloon 100 before the balloon 100 is expanded and when being pre-expanded. Specifically, the expansion cover 220 is movably sleeved outside the pushing catheter 310, and accommodates the balloon 100 before the expansion and during the pre-expansion of the balloon 100. The expansion cover 220 is a sleeve structure having an opening. The proximal end portion of the expansion cover 220 may be a shape that is convex toward the proximal end, such as a conical shape, an arc shape, or the like, or a flush structure in which the proximal end surface is perpendicular or approximately perpendicular to the central axis, or may be a concave structure that is concave toward the distal end. Specifically, in this embodiment, the proximal end portion of the expansion cover 220 has a conical structure to improve the fitting between the expansion cover 220 and the proximal end portion of the balloon 100.

The pre-expansion mechanism 200 of the DCB catheter 1000 includes a connecting member 240 coupled to the expansion cover 220. The connecting member 240 connects the expansion cover 220, and moves axially relative to the pushing catheter 310 after the balloon 100 is pre-expanded to expose the balloon 100 outside the expansion cover 220. Specifically, in this embodiment, the connecting member 240 is a connecting tube. The connecting tube is a hollow tubular structure having a certain axial length. In an embodiment, the expansion cover 220 and the connecting member 240 may be connected by a conventional connecting manner such as a bonding connection, a threaded connection, a soldering, an interference fit, and the like. Optionally, the expansion cover 220 is detachably connected to the connecting member 240 to facilitate replacing the expansion cover 220. It can be understood that in other embodiments, the expansion cover 220 and the connecting member 240 can also be integrally formed. The connecting member 240 is movably sleeved outside the pushing catheter 310, and both the expansion cover 220 and the connecting member 240 are movable along the axial direction of the pushing catheter 310. It can be understood that in other embodiments, the connecting member 240 can also be at least two connecting wires having a certain length, and consequently the expansion cover 220 can be operated to advance or retract by the connecting wires. It will also be appreciated that in other embodiments, the connecting member 240 may also be at least one solid connecting rod. In order to smoothly operate the advancement or retraction of the expansion cover 220, the number of connecting rods is optionally at least two, and in order to reduce the overall outer diameter profile of the entire device, the connecting rod is particularly a flat rod-shape structure to better fit the outer wall of the pushing catheter 310. Referring to FIG. 3 and FIG. 4 together, before the balloon 100 is pre-expanded, the expansion cover 220 is sleeved on the outside of the balloon 100 and is folded and twisted together with the balloon 100 before the pre-expansion to form a cylinder, such as a circular cylinder or a prism. The process of folding and twisting can be performed on a machine such as a balloon folding machine.

Referring to FIG. 3 to FIG. 6 together, after the expansion cover 220 and the balloon 100 are both sent into the lesion segment, the balloon 100 is filled and drives the expansion cover 220 to expand, and the expansion cover 220 pre-expands the blood vessel at the lesion segment. An inner diameter of the expanded expansion cover 220 is consistent with or slightly larger than a diameter of the balloon 100 after the pre-expansion. Optionally, an inner diameter of the expanded expansion cover 220 is larger than a diameter of the pre-expanded balloon 100 by 0 to 0.10 mm. The purpose of the configuration is that, the balloon 100 can be smoothly accommodated in the expansion cover 200, and also drives the expansion cover 220 covering the outside of the balloon 100 to simultaneously expand during the pre-expansion.

Figure 7:
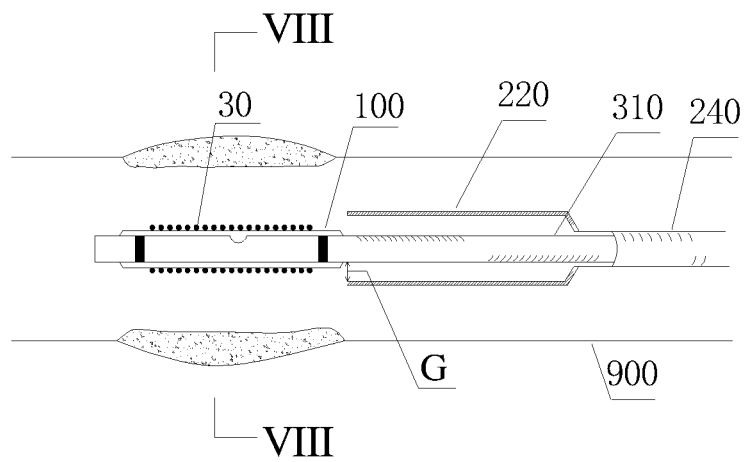
FIG. 7 is a schematic diagram of the DCB catheter of FIG. 1 after the expansion cover moves towards one end away from the balloon.
Figure 8:
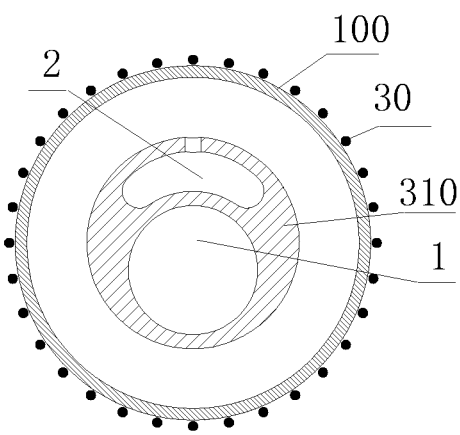
FIG. 8 is a cross-sectional diagram of the DCB catheter of FIG. 7 along the line VIII-VIII.
Figure 9:
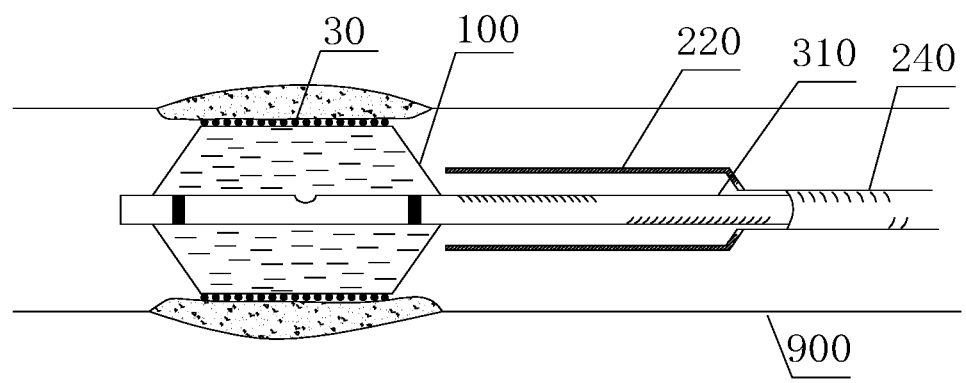
FIG. 9 is a schematic structural diagram of the balloon of the DCB catheter of FIG. 1 that is expanded again after the pre-expansion.

Referring to FIG. 7 to FIG. 9 together, after the pre-expansion is completed, the expansion cover 220 is retracted away from the balloon 100, so that the balloon 100 is exposed outside the expansion cover 220. That is, the balloon 100 is exposed to the vascular environment. Subsequently, the balloon 100 is filled again, and the balloon 100 expands and treats the blood vessel of the lesion segment, and the drug coating 30 on the surface of the balloon 100 is eluted from the surface of the balloon 100 and delivered to the inner wall of the blood vessel.

It can be understood that in the present embodiment, the balloon 100 is pressure relieved after the pre-expansion is completed, so that a gap G is formed between the balloon 100 and the expansion cover 220. When the gap G between the balloon 100 and the expansion cover 220 is less than a preset threshold, the balloon 100 is accommodated in the expansion cover 220. When the gap G between the balloon 100 and the expansion cover 220 is greater than the preset threshold, the connecting member 240 can move toward the end away from the balloon 100 with respect to the pushing catheter 310 to expose the balloon 100 outside the expansion cover 220. The preset threshold is approximately 0 mm-10 mm.

Both the balloon 100 and the expansion cover 220 are made of a soft material with a certain elastic modulus. As such, the balloon 100 and the expansion cover 220 can be folded and twisted together on the balloon folding machine without expansion or inflation. The material of a first expansion cover 220 has an elastic modulus that is less than the elastic modulus of the material from which the balloon 100 is made. Therefore, when the two are subjected to the same external pressure, the degree of deformation of the balloon 100 is larger than the degree of deformation of the expansion cover 220. After the external pressure disappears, the speed of the balloon 100 restoring to its initial shape is also faster than the speed of the expansion cover 220 restoring to its initial state. Therefore, after the balloon 100 and the expansion cover 220 sleeved on the outside of the balloon 100 are both pushed together to the blood vessel wall of the lesion segment, the pressurized liquid is introduced into the interior of the balloon 100, and the balloon 100 when filled and expanded may drive the expansion cover 220 sleeved on the outside of the balloon 100 to expand simultaneously. Both the balloon 100 and the expansion cover 220 expand together till the expansion cover 220 fits the blood vessel wall of the lesion segment to achieve the pre-expansion of the inner wall of the blood vessel. After the pre-expansion is completed, the balloon 100 is pressure relieved or incompletely pressure relieved, the balloon 100 will return to the initial state or an incompletely expanded state at a faster speed, and the expansion cover 220 will return to the initial state or an incompletely expanded state at a slower speed. At this time, a large gap G is generated between the balloon 100 and the first expansion cover 220, and the operator only needs to retract the first expansion cover 220 to the proximal end, so that the balloon 100 is exposed to the lesion segment. After that, the balloon 100 can be refilled, the balloon 100 expands the blood vessel wall of the lesion segment, and the drug coating 30 is eluted from the surface of the balloon 100 and delivered to the inner wall of the blood vessel to realize treatment of the lesion segment. The expansion cover 220 is optionally made of a material such as silica gel, polyurethane, or polyether amide, and is not limited specifically, as long as the elastic modulus of the expansion cover 220 is less than the elastic modulus of the balloon 100.

Referring again to FIG. 1, the proximal end of the connecting member 240 is provided with a handle 230. The handle 230 moves axially with respect to the catheter set 320. As such, by holding the handle 230 by hands, the user can operate the expansion cover 220 to retract to the proximal end or push to the distal end.

Figure 5:
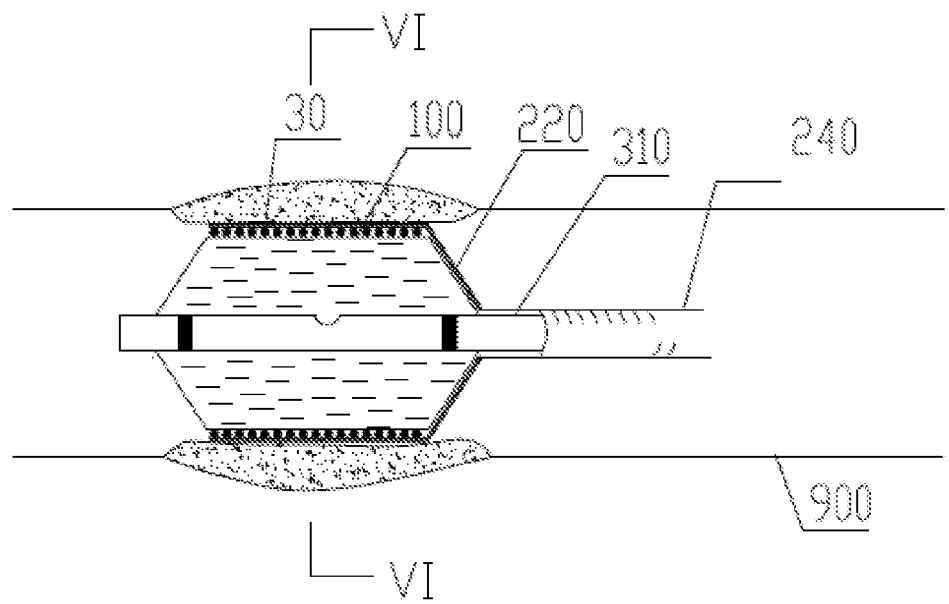
FIG. 5 is a schematic diagram of the DCB catheter of FIG. 1 after the balloon is pre-expanded.
Figure 6:
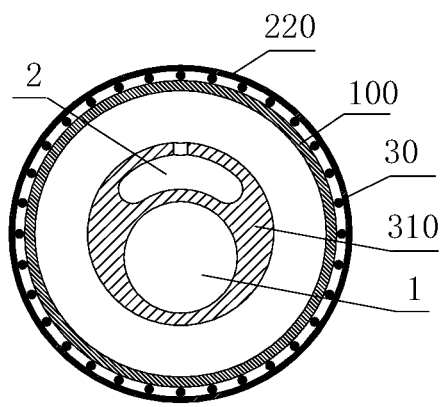
FIG. 6 is a cross-sectional diagram of the DCB catheter of FIG. 5 along the line VI-VI.

As shown in FIG. 3 to FIG. 9, an implementation process of the DCB catheter 1000 according to an embodiment of the present disclosure is illustrated. Referring to FIG. 3, the DCB catheter 1000 is first pushed to the diseased blood vessel where an expansion is desired. Referring to FIG. 5, the pressurized liquid is introduced into the inner cavity of the balloon 100 to fill the balloon 100 and to drive the expansion cover 220 sleeved outside the balloon 100 to simultaneously expand till the expansion cover 220 fits the blood vessel wall of the lesion segment to apply the pre-expansion to the stenosis of the blood vessel lesion segment. Referring to FIG. 7, after the pre-expansion is completed, the filling liquid is pumped out by the balloon pressure pump, and the balloon 100 is gradually pressure relieved to the initial empty state or an incompletely expanded state. At this time, because the elastic modulus of the material from which the expansion cover 220 is made is smaller than the elastic modulus of the material from which the balloon 100 is made, the balloon 100 will return to the initial state or the incompletely expanded state at a faster speed, and the expansion cover 220 will return to the initial state or the incompletely expanded state at a slower speed. When a relatively large gap is formed between the balloon 100 and the expansion cover 220, the operator can retract the expansion cover 220 towards the proximal end, exposing the balloon 100 in the blood vessel. Referring to FIG. 9 again, the balloon 100 is filled again, and the balloon 100 expands the blood vessel wall of the lesion segment, meanwhile the drug coating 30 is eluted from the surface of the balloon 100 and delivered to the inner wall of the blood vessel to realize treatment of the lesion segment.

Figure 10:
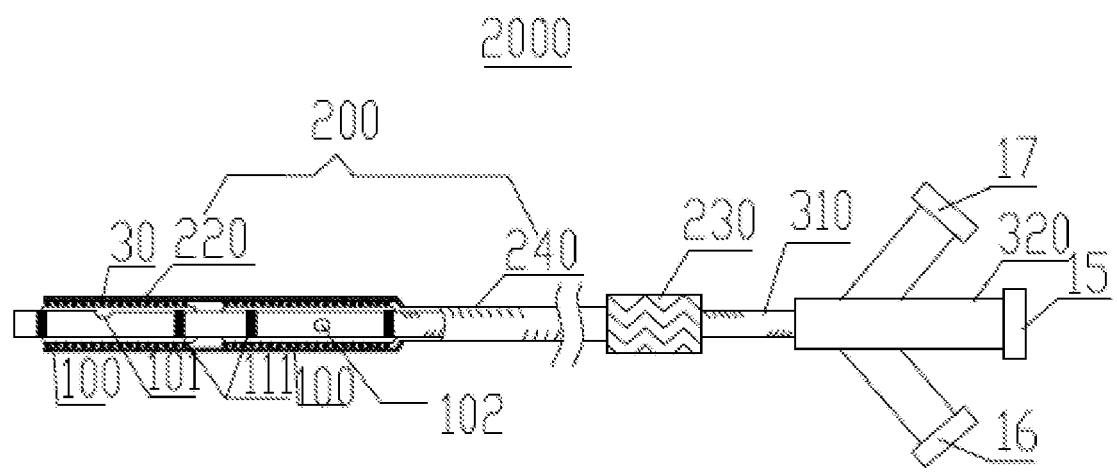
FIG. 10 is a schematic structural diagram of the DCB catheter according to a second embodiment of the present disclosure.

As shown in FIG. 10, a DCB catheter according to a second embodiment of the present disclosure is provided. In the second embodiment, the structure of the DCB catheter 2000 is similar to the structure of the DCB catheter 1000 of the first embodiment. Therefore, the dimensions of the components, the component names, the positional relationships of the components, and the like that are included in the DCB catheter 2000, can be referred to the DCB catheter 1000, and will not be repeated here. The difference is that, the DCB catheter 2000 includes two drug-coated balloons 100 fixedly disposed at the distal end of the pushing catheter 310, the catheter set 320 is provided with two filling ports 16 and 17, and the interior of the pushing catheter 310 is axially provided with two filling cavities 2. It can be understood that in other embodiments, the number of balloons 100 can also be set to multiple. Optionally, a plurality of balloons 100 are connected in series and fixedly disposed on the pushing catheter 310, i.e., a plurality of balloons 100 are coaxially disposed for treating multiple lesion segments of the same blood vessel.

Specifically, referring to FIG. 10, the distal end of the pushing catheter 310 is provided with two balloons 100 to simultaneously expand and treat multiple lesion segments. The pushing catheter 310 passes through the two balloons 100 in the axial direction successively, and is in a sealed connection with both balloons 100. The relative position between the two balloons 100 is not limited, as long as both are located at the distal end of the pushing catheter 310. The two balloons 100 can be next to each other or spaced apart. The shapes of the two balloons 100 can be the same or different. The shapes of the two balloons 100 are usually cylindrical or spherical. The diameters of the two balloons 100 are selected according to the diameter of the diseased blood vessel to be treated, and the diameters of the two balloons may be the same or different. The DCB catheter with the two balloons 100 provided in this embodiment can not only simultaneously treat different lesions, but also, when one of the balloons 100 is first filled, the filled balloon 100 also blocks blood flow, thereby preventing the drug coating 30 on the surface of the other balloon 100 from being washing away by blood flow. In this case, the surface of the first filled balloon 100 may not be provided with an active drug coating to reduce the cost of the device.

It can be understood that, in an embodiment, each of the balloons 100 is accommodated in the same expansion cover 220 before the expansion, and each balloon 100 is folded and twisted together with the expansion cover 220 to form a cylinder. In another embodiment, each balloon 100 is accommodated in a corresponding expansion cover 220 before the expansion, i.e., each balloon 100 is sleeved with an expansion cover 220. Optionally, each balloon 100 is respectively accommodated in the corresponding expansion cover 220 before the pre-expansion, and is folded and twisted together with the corresponding expansion cover 220 to form a cylinder.

Specifically, the expansion cover 220 is movably sleeved on the pushing catheter 310 and is sleeved outside the corresponding balloon 100. The number of expansion covers 220 is equal to or less than the number of balloons 100. Specifically, in an embodiment, two balloons 100 are commonly accommodated in an expansion cover 220. In another embodiment, when the two balloons 100 are separated from each other relatively far apart, each balloon 100 is correspondingly provided with an expansion cover 220, i.e., two expansion covers 220 are respectively and correspondingly sleeved outside the two balloons 100.

It can be understood that, in an embodiment, the pre-expansion mechanism 200 includes only one connecting member 240, and the connecting member 240 moves axially with respect to the pushing catheter 310 after at least one of the balloons 100 is pre-expanded, so that each balloon 100 is exposed outside the expansion cover 220. In another embodiment, the pre-expansion mechanism 200 includes a plurality of connecting members 240 that are in one-to-one correspondence with the plurality of expansion covers 220. Each of the connecting members moves axially with respect to the pushing catheter 310 after the corresponding balloon 100 is pre-expanded, so that the balloon 100 is exposed outside the corresponding expansion cover 200.

Specifically, in an embodiment, two expansion covers 220 are connected by a connecting member 240. In another embodiment, each expansion cover 220 is provided with a corresponding connecting member 240. As such, after the entire device (i.e., the DCB catheter 2000) reaches the lesion segment, two balloons 100 can be simultaneously filled and drive two expansion cover 220 to expand together, then the two balloons 100 are simultaneously pressure relieved, and then the two expansion covers 220 are simultaneously retracted outside the patient's body. It can be understood that in this embodiment, it is optional that the diameter of the connecting member 240 located between the two expansion covers 220 is slightly larger than the outer diameter of the balloon 100 located closer to the proximal end, so that the connecting member 240 can be smoothly retracted.

It can be understood that in other embodiments, the two expansion covers 220 can also be connected by at least two connecting wires or at least one solid rod. The expansion cover 220 at the proximal end can also be connected to the handle 230 via at least two connecting wires or at least one solid rod. In other words, each connecting member 240 can have a hollow tubular structure, a filamentary structure, or a solid rod-shape structure.

Figure 11:
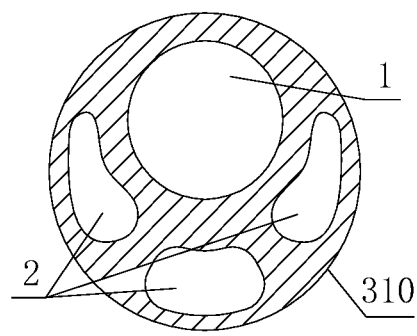
FIG. 11 is a schematic structural diagram of the pushing catheter of the DCB catheter of FIG. 10 according to a first implementation.

As shown in FIG. 11, at least two first filling cavities 2 are axially disposed within the pushing catheter 310, and the inner cavity of each balloon 100 is in communication with at least one filling cavity 2, respectively. The pushing catheter 310 can be formed by integrally molding a multi-lumen tube or by assembling a plurality of separate tubes.

Referring to FIG. 11, the pushing catheter 310 is an integrally molded multi-lumen tube, and the pushing catheter 310 is axially provided with a guide wire cavity 1 and three filling cavities 2 which are separated from each other. Two filling cavities 2 are in communication with the inner cavity of one of the balloons 100, and the third filling cavity 2 is in communication with the inner cavity of another balloon 100. Any two out of the guide wire cavity 1 and the three filling cavities 2 are disposed in parallel. The cross-sectional shape of the multi-lumen tube is not limited, as long as a plurality of functional cavities are parallel to each other. The guide wire cavity 1 is used for accommodating the guide wire. Therefore, the guide wire cavity 1 requires a smooth cavity and a shape to facilitate the movement of the guide wire. Generally, the cross section of the guide wire cavity 1 has a circular or elliptical shape. The cross-sectional shape of the filling cavity 2 is not limited and may be any shape, and is generally arranged according to the cross-sectional shape of the pushing catheter 310, the position and shape of the guide wire cavity 1, and the filling cavity 2 having the largest cross-sectional area.

Figure 12:
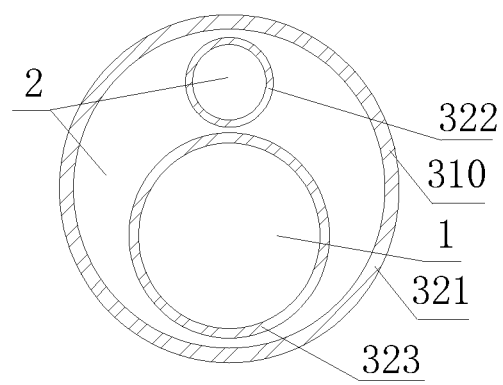
FIG. 12 is a schematic structural diagram of the pushing catheter of the DCB catheter of FIG. 10 according to a second implementation.

Referring to FIG. 12, the pushing catheter 310 includes an outer tube 321 and two inner tubes 322 and 323 sleeved within the outer tube. The lumen of one inner tube 322 serves as a guide wire cavity 1, and the space between the inner tube 322 and the outer tube 321 and the other inner tube 323 serve as two filling cavities 2, respectively. In addition to the above structure, the pushing catheter 310 can have multiple tubes sleeved to form corresponding guide wire cavity 1 and filling cavity 2. It can be understood that, in other embodiments, the specific structure of the pushing catheter 310 is not limited to the above embodiments, and may be various structures capable of forming the guide wire cavity 1 and the filling cavity 2.

Referring again to FIG. 10, the proximal end of the pushing catheter 310 is provided with a catheter set 320. The catheter set 320 is provided with a guide wire port 15, two filling ports 16 and 17. The guide wire port 15 is in communication with the guide wire cavity 1. A guide wire (not shown) is insertedly mounted within the passage formed by the guide wire port 15 and the guide wire cavity 1. A tube located in one of the balloons 100 of the pushing catheter 310 is provided with a balloon filling port 101. A tube located in another one of the balloons 100 of the pushing catheter 310 is provided with a balloon filling port 102. Both ends of a filling cavity 2 are connected to the filling port 16 and the balloon filling port 101, respectively. Both ends of another filling cavity 2 are connected to the filling port 17 and the balloon filling port 102, respectively. As such, the filling port 16, the filling cavity 2, and the balloon filling port 101 form a passage for filling and pressure relieving for one of the balloons 100. The filling port 17, the filling cavity 2, and the balloon filling port 102 form a passage for filling and pressure relieving for another one of the balloons 100.

The DCB catheter of the present disclosure has at least the following beneficial effects over the prior art:

(1) The expansion cover is sleeved outside the balloon, and is transported to the lesion segment together with the balloon, and then the expansion cover expands so as to apply effective pre-expansion to the lesion segment;

(2) The expansion cover protects the drug coating on the surface of the balloon so as to reduce the drug loss during the transporting process;

(3) can use multiple balloons to treat multiple segments of lesion at one time;

(4) The balloon at the proximal end may serve as a blocking balloon to temporarily block the blood flow in the blood vessel, further preventing the flushing of the active drug coating on the surface of the balloon at the distal end by the blood, reducing the drug loss, improving the drug amount delivered from the balloon surface to the blood vessel wall as well as the efficiency.

Figure 13:
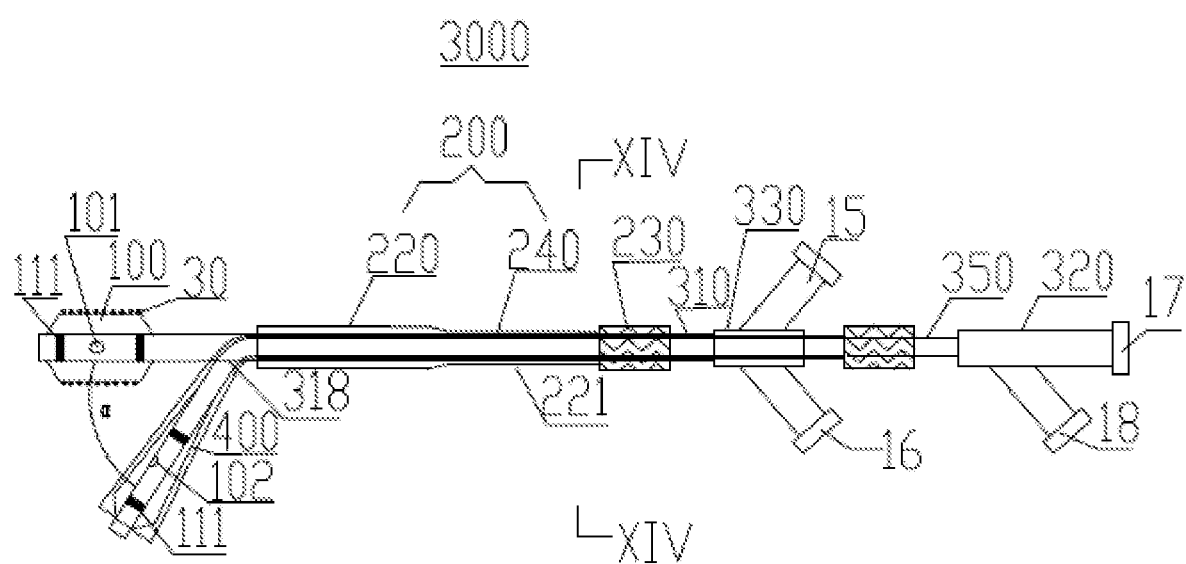
FIG. 13 is a schematic structural diagram of the DCB catheter according to a third embodiment of the present disclosure.

As shown in FIG. 13, a DCB catheter according to a third embodiment of the present disclosure is provided. In the third embodiment, the structure of the DCB catheter 3000 is similar to the structure of the DCB catheter 2000 of the second embodiment. Therefore, the dimensions of the components, the component names, the positional relationships of the components, and the like that are included in the DCB catheter 3000, can be referred to the DCB catheter 2000, and will not be repeated here. The difference is that, the DCB catheter 3000 also includes a sliding catheter 350 that slides relative to the pushing catheter 310, with one DCB 100 fixedly disposed on the pushing catheter 310 and another DCB 400 fixedly disposed on the sliding catheter 350. It can be understood that in other embodiments, the number of balloons may be set to multiple and the distance between the plurality of balloons may be adjusted. In this embodiment, when the DCB catheter 3000 is under pressure and filled, there is an angle α between the axial directions of the two balloons 100 and 400, i.e., the two balloons 100 and 400 are not coaxially arranged, that is, an angle α is formed between the axis of the balloon 100 and the axis of the balloon 400, for the treatment of different branch vascular lesions of a bifurcated blood vessels.

Specifically, referring to FIG. 13, in the embodiment, the DCB catheter 3000 includes a pushing catheter 310, a balloon 100 disposed at a distal end of the pushing catheter 310, a pre-expansion mechanism 200, a sliding catheter 350, and a balloon 400 disposed at a distal end of the sliding catheter 350. At least part of the surfaces of the balloon 100 and balloon 400 are covered with a drug coating 30. The pre-expansion mechanism 200 includes an expandable expand cover 220 that is movably sleeved outside of the balloon 100, and a connecting member 240 that is coupled to the expansion cover 220. The connecting member 240 is sleeved on the outside of the pushing catheter 310 and moves axially relative to the pushing catheter 310. The structures of the balloon 100 and the expansion cover 220 and the mutual positional relationship and the connection relationship are the same as those in the first embodiment, and details are not described herein again.

At least one balloon 400 is provided at the distal end of the sliding catheter 350. A guide wire cavity 1 and a filling cavity 2 are axially disposed inside the pushing catheter 310 of the DCB catheter 3000. An internal lumen 324 can also be provided in the push catheter 310, and the sliding catheter 350 is movably mounted within the internal lumen 324 of the pushing catheter 310. The distal end of the sliding catheter 350 extends out of the wall of the pushing catheter 310 near the distal end. The manner of extending out may be: a through hole 318 is provided on a side wall at the distal end of the pushing catheter 310, and a side hole 221 is correspondingly provided on the tube body of the connecting member 240. The term "correspondingly" refers to, when the distal end portion of the expansion cover 220 is sleeved on the distal end portion of the balloon 100, the through hole 318 coincides with the side hole 221 mutually. At this time, the distal end of the sliding catheter 350 extends through the through hole 318 and the side hole 221 and is connected to the proximal end of the balloon 400. Since the sliding catheter 350 can slide axially on the pushing catheter 310, the distance between the balloon 400 disposed at the distal end of the sliding catheter 350 and the balloon 100 disposed at the distal end of the pushing catheter 310 can be adjusted to accommodate different branch vascular lesions of a bifurcated blood vessels.

It can be understood that in other embodiments, the distal end of the pushing catheter 310 and the distal end of the sliding catheter 350 can also respectively extend out of a branch tube body of a bifurcated tube (such as a Y-shaped tube having at least two branches). At this time, the sliding catheter 350 can also slide along the axial direction within the pushing catheter 310, so that the distance between the balloon 400 and the balloon 100 can be adjusted to treat the bifurcated blood vessel.

It is also understood that in other embodiments, a bifurcated tube (such as a Y-shaped tube having at least two branches) may be disposed at the distal end of the pushing catheter 310, and the distal end of the sliding catheter 350 extends out of one of the branch tube bodies. At this time, the sliding catheter 350 can also slide along the axial direction within the pushing catheter 310, so that the distance between the balloon 400 and the balloon 100 can be adjusted to treat the bifurcated blood vessel. However, in order to avoid affecting the retracting of the expansion cover 220 after the expansion towards the proximal end, the surface of the expansion cover 220 should be set to a tearable form, such as a point breaking line, and the point breaking line is optionally corresponding to the bifurcation of the bifurcated tube. As such, when the expansion cover 220 is retracted, the point breaking line can be gradually torn from the bifurcation, which facilitates the retraction of the expansion cover 220.

It can be understood that in the embodiment, the pre-expansion mechanism 200 includes an expansion cover 220. The balloon 100 and the balloon 400 are both accommodated in the same expansion cover 220 before the expansion and during the pre-expansion, and the balloon 100 and the balloon 400 are folded and twisted together with the expansion cover 220 to form a cylinder.

Figure 14:
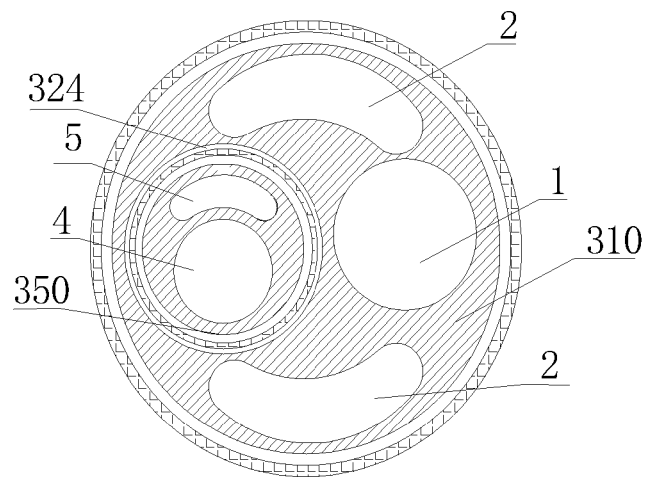
FIG. 14 is a cross-sectional diagram of the DCB catheter of FIG. 13 along the line XIV-XIV.

In an embodiment, the pre-expansion mechanism 200 includes a connecting member 240 that connects to the expansion cover 220. The connecting member 240 moves axially relative to the pushing catheter 310 after the balloon 100 is pre-expanded so that each balloon 100 and 400 is exposed outside the expansion cover 220, or moves axially relative to the sliding catheter 350 after the balloon 400 is pre-expanded so that each balloon 100 and 400 is exposed outside the expansion cover 220. As shown in FIG. 14, a guide wire cavity 4 and a filling cavity 5 are disposed along the axial direction of the sliding catheter 350. The guide wire cavity 4 extends through the proximal end and the distal end of the sliding catheter 350 for accommodating the guide wire. The filling cavity 5 is in communication with the interior of the balloon 400 for filling and pressure relieving of the balloon 400.

The proximal end of the sliding catheter 350 is also provided with a catheter set 330. That is, the catheter set 330 is also movably sleeved outside of the pushing catheter 310 and moves axially relative to the pushing catheter 310. The proximal end of the catheter set 330 is provided with a guide wire port 17 and a filling port 18. The guide wire port 17 is connected to the proximal end of the guide wire cavity 4. The filling port 18 is connected to the proximal end of the filling cavity 5.

The balloon 400 is fixed to the distal end of the sliding catheter 350 by welding, bonding, or the like. At least a portion of the outer surface of the balloon 400 is covered with a drug coating 30. The structure of the balloon 400 is basically the same as the structure of the balloon 100 of the first embodiment, and details are not described herein again.

It can also be understood that in other embodiments, the structure of the balloon 400 may be different from the structure of the balloon 100 of the first embodiment. Specifically, referring to FIG. 13, the diameter of the portion of the balloon 400 near the proximal end gradually decreases from the distal end to the proximal end. There are various implementations of this progressively reducing structure. For example, the balloon 400 is generally conical, i.e., a substantially conical shape having a small proximal end diameter and a large distal end diameter. Or the proximal end portion and the distal end portion of the second balloon 400 are substantially conical, the middle portion is cylindrical, and there is a smooth transition between the cylindrical and the conical. Or the proximal end portion and the distal end portion of the balloon 400 are substantially conical, the central portion is cylindrical, and the diameters between the cylindrical and the conical are different to form a hierarchicstructure. The conical structure of the proximal end portion of the balloon 400, is generally long tapered, i.e., the taper changes little to form a long length cone with little changed diameter, and the diameter of the taper portion is much smaller than the cylindrical portion. The tapered, long-tapered structure can increase the distance between the balloon 100 and the balloon 400, avoiding the problems of excessive vascular dilation, tearing of the blood vessels or formation of a vascular dissection when the two are fitted or the distance is too small after the filling, meanwhile increasing the effective length of the working portion after the balloon is filled and expanded.

Figure 15:
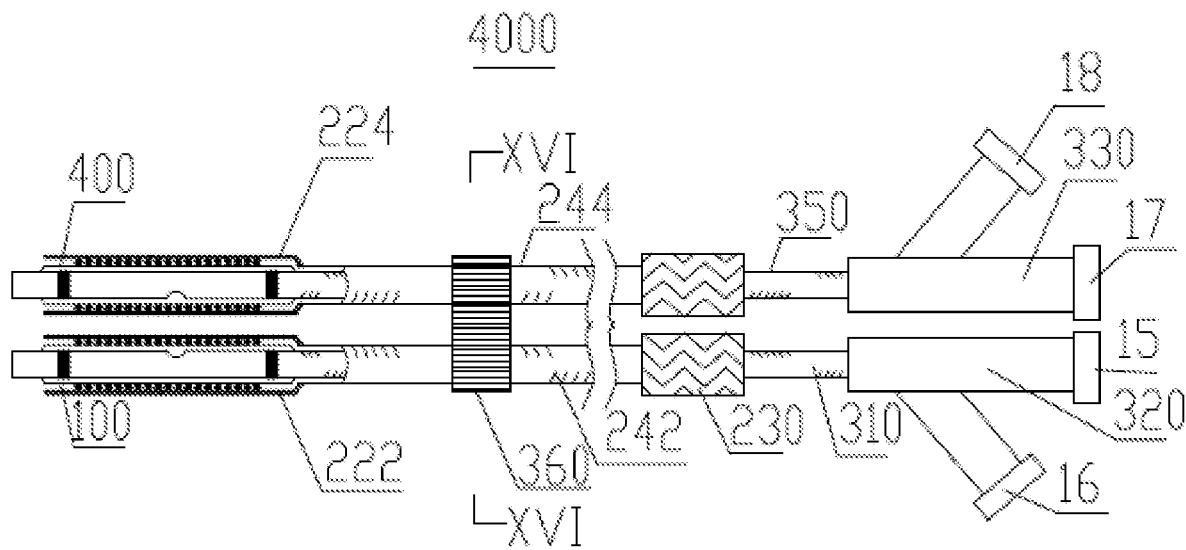
FIG. 15 is a schematic structural diagram of the DCB catheter according to a fourth embodiment of the present disclosure.
Figure 16:
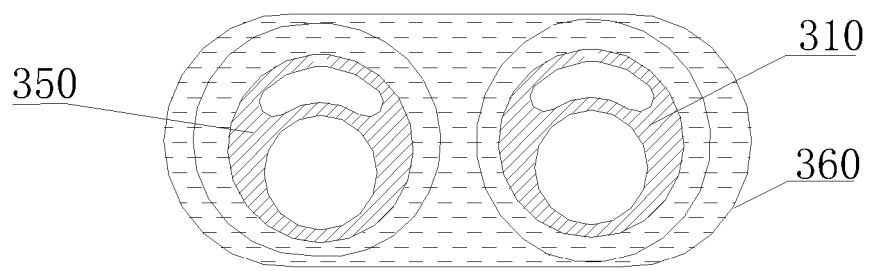
FIG. 16 is a cross-sectional diagram of the DCB catheter of FIG. 15 along the line XVI-XVI.

Referring to FIG. 15 and FIG. 16 together, a DCB catheter according to a fourth embodiment of the present disclosure is provided. In the fourth embodiment, the structure of the DCB catheter 4000 is similar to the structure of the DCB catheter 3000 of the third embodiment. Therefore, the dimensions of the components, the component names, the positional relationships of the components, and the like that are included in the DCB catheter 4000, can be referred to the DCB catheter 3000, and will not be repeated here. The difference is that, the DCB catheter 4000 also includes a limiter 360 for connecting the pushing catheter 310 and the sliding catheter 350, the pushing catheter 310 and the sliding catheter 350 are disposed substantially in parallel, and the two balloons 100 and 400 are axially parallel.

Specifically, as shown in FIG. 15 and FIG. 16, in the present embodiment, the sliding catheter 350 can also be disposed substantially parallel to the pushing catheter 310, the sliding catheter 350 and the pushing catheter 310 are connected by a limiter 360 between them. The limiter 360 can allow only axial relative movement between the pushing catheter 310 and the sliding catheter 350, while forbidding radial deviation. The limiter 360 has various implementations: for example, the limiter 360 may be a collar or a hoop member disposed between the pushing catheter 310 and the sliding catheter 350, and the pushing catheter 310 and the sliding catheter 350 are together movably insertedly mounted within the collar or the hoop member, thereby requiring only axial movement between the two. The limiter 360 can also be a tubular body having a certain axial length, or a third tubular body in which the pushing catheter 310 and the sliding catheter 350 are sleeved together. The specific shape and axial length of the limiter 360 are not limited and can be adjusted according to the lengths of the pushing catheter 310 and the sliding catheter 350. For example, the limiter 360 can be round, elliptical or in a shape of a digital figure eight. It will be understood that, in order to reduce the overall diameter of the DCB catheter, the shapes of the pushing catheter 310 and the sliding catheter 350 optionally cooperate to form a complete, no angular shape, such as circular or elliptical.

Referring to FIG. 15, in the present embodiment, the pre-expansion mechanism 200 includes expansion covers 222 and 224 that are in one-to-one correspondence with the balloon 100 and the balloon 400. The balloon 100 is accommodated in one of the expansion covers 222 prior to the pre-expansion and is folded and twisted together with the expansion covers 222 to form a cylinder. The balloon 400 is accommodated in another one of the expansion covers 224 prior to the pre-expansion and is folded and twisted together with the expansion cover 224 to form a cylinder. The structures of the expansion covers 222 and 224 are substantially the same as that of the expansion cover 220, and will not be described herein. The expanded expansion cover 224 has an inner diameter that is the same as or slightly larger than the diameter of the expanded balloon 400.

The pre-expansion mechanism 200 includes a plurality of connecting members 242 and 244 that are in one-to-one correspondence with the expansion covers 222 and 224. In this embodiment, one of the connecting members 242 moves axially relative to the pushing catheter 310 after the balloon 100 is pre-expanded to expose the balloon 100 to the outside of the expansion cover 222, or another connecting member 244 moves axially relative to the sliding catheter 350 after the balloon 400 is pre-expanded to expose the balloon 400 to the outside of the expansion cover 224.

Specifically, the proximal end of the expansion cover 224 is provided with a connecting tube 244. The connecting tube 244 is movably sleeved outside of the sliding catheter 350 and moves axially relative to the sliding catheter 350. The connecting tube 244 and the sliding catheter 350 are sleeved together and are insertedly mounted together in the inner lumen of the pushing catheter 310, and simultaneously extend out of the through hole of the side wall of the distal end of the pushing catheter 310. Both the expansion cover 224 and the balloon 400 can move relative to the balloon 100 and the expansion cover 222 to adjust the mutual positional relationship between them. The connecting tube 244 can also be selected from other implementations such as a filament structure or a solid rod structure, and details are not described herein again.

The DCB catheter of this embodiment has at least the following beneficial effects over the prior art:

(1) The expansion covers are sleeved outside two balloons respectively, and are transported to the lesion segment together with the two balloons, and then the expansion covers expand so as to apply effective pre-expansion to the lesion segments;

(2) The expansion cover protects the drug coating on the surface of the balloons so as to reduce the drug loss during the transportation process;

(3) the relative position between the two balloons is adjustable, to better accommodate several branch vessels of a bifurcated blood vessel and different lesion locations;

(4) one of the balloons is set to be irregular to prevent tearing the blood vessel at the bifurcation.

Overall, the DCB catheter of the present disclosure, by disposing a pre-expansion mechanism on the outside of the DCB, and by transporting the pre-expansion mechanism and the DCB together to the lesion segment, may effectively protect the DCB from being flushed by blood flow, reducing the drug loss during the transportation process; the pre-expansion mechanism applies the pre-expansion to the lesion segment, allowing the DCB to smoothly enter into the lesion, thereby increasing the area of the inner wall of the blood vessel at the lesion segment that may contact the surface of the DCB, and increasing the amount of medication delivered to the blood vessel wall after the expansion of the DCB, improving the therapeutic effect; no need to use additional pre-expanded balloons, reducing the complexity of surgery and the cost of surgery, and save operation time.

The foregoing implementations are merely specific embodiments of the present disclosure, and are not intended to limit the protection scope of the present disclosure. It should be noted that any variation or replacement readily figured out by persons skilled in the art within the technical scope disclosed in the present disclosure shall all fall into the protection scope of the present disclosure. Therefore, the protection scope of the present disclosure shall be subject to the protection scope of the claims.

What is claimed is:

1. A drug-coated balloon (DCB) catheter, comprising:
a pushing catheter;
a first balloon fixedly disposed on the pushing catheter; and
a pre-expansion mechanism comprising:
an expansion cover for accommodating the first balloon before the first balloon is expanded and when the first balloon is being pre-expanded, and
a connecting member that connects the expansion cover and moves axially with respect to the pushing catheter after the first balloon is pre-expanded so as to expose the first balloon outside the expansion cover;
wherein before the first balloon is pre-expanded, the expansion cover is sleeved outside the first balloon and is folded and twisted together with the first balloon to form a first cylinder.

2. The DCB catheter according to claim 1, wherein the first balloon is pressure relieved after the pre-expansion is completed so as to form a gap between the first balloon and the expansion cover.

3. The DCB catheter according to claim 2, wherein when the gap between the first balloon and the expansion cover is smaller than a preset threshold, the first balloon is accommodated in the expansion cover; when the gap between the first balloon and the expansion cover is larger than the preset threshold, the connecting member moves with respect to the pushing catheter towards one end away from the first balloon so as to expose the first balloon outside the expansion cover.

4. The DCB catheter according to claim 3, wherein the preset threshold is 0 mm-10 mm.

5. The DCB catheter according to claim 1, wherein the first balloon before the pre-expansion is provided with a plurality of flaps.

6. The DCB catheter according to claim 1, wherein an inner diameter of the expanded expansion cover is equal to or larger than an outer diameter of the first balloon after the pre-expansion.

7. The DCB catheter according to claim 1, wherein the expansion cover is made of a material having an elastic modulus smaller than an elastic modulus of the material from which the first balloon is made.

8. The DCB catheter according to claim 1, wherein a number of the first balloons is one or a plurality, the number of the expansion covers is equal to or less than the number of the first balloons.

9. The DCB catheter according to claim 8, wherein when the number of the expansion covers is one, each of the first balloons is accommodated in a same expansion cover; when the number of the expansion covers is a plurality, each of the first balloons is accommodated in a corresponding expansion cover respectively.

10. The DCB catheter according to claim 1, wherein the pushing catheter is provided axially with a first guide wire cavity and a first filling cavity, the first guide wire cavity is through connected with the pushing catheter and the first balloon, a distal end of the first filing cavity is connected with an inside of the first balloon.

11. The DCB catheter according to claim 10, wherein the DCB catheter further comprises a catheter set disposed at a proximal end of the pushing catheter, the catheter set is provided with a first guide wire port connected with the first guide wire cavity and a first filling port connected with the first filling cavity.

12. The DCB catheter according to claim 11, wherein the DCB catheter further comprises a handle disposed at a proximal end of a connecting tube of the expansion cover, the handle moves axially with respect to the catheter set.

13. The DCB catheter according to claim 1, wherein the DCB catheter further comprises a sliding catheter slidably connected with the pushing catheter, the sliding catheter is provided with a second balloon, a relative position of the second balloon with respect to the first balloon is adjustable.

14. The DCB catheter according to claim 13, wherein the sliding catheter is movably insertedly mounted within the pushing catheter, and a distal end of the sliding catheter extends out of a wall of the pushing catheter near a distal end.

15. The DCB catheter according to claim 13, wherein a proximal section of the sliding catheter is disposed in parallel with a proximal section of the pushing catheter.

16. The DCB catheter according to claim 13, wherein the first balloon and the second balloon are coaxially disposed and connected in series.

17. The DCB catheter according to claim 13, wherein an axis of the first balloon and an axis of the second balloon forms an angle.

18. The DCB catheter according to claim 13, wherein the first balloon before being expanded and the second balloon before being expanded are both accommodated in the expansion cover, and are folded and twisted together with the expansion cover to form a second cylinder.

19. The DCB catheter according to claim 13, wherein the expansion cover comprises a first expansion cover and a second expansion cover, the first balloon is accommodated in the first expansion cover before the first balloon is pre-expanded and folded and twisted together with the first expansion cover to form a third cylinder; the second balloon is accommodated in the second expansion cover before the second balloon is pre-expanded and folded and twisted together with the second expansion cover to form a fourth cylinder.

20. The DCB catheter according to claim 19, wherein the connecting member comprises a first connecting member connected with the first expansion cover and a second connecting member connected with the second expansion cover, the first connecting member moves axially with respect to the pushing catheter after the first balloon is pre-expanded so as to expose the first balloon outside the first expansion cover; the second connecting member moves axially with respect to the pushing catheter after the second balloon is pre-expanded so as to expose the second balloon outside the second expansion cover.

21. The DCB catheter according to claim 19, wherein the connecting member is connected to the first expansion cover and the second expansion cover, the connecting member moves axially with respect to the pushing catheter or the sliding catheter after the first balloon and/or the second balloon is pre-expanded so as to expose the first balloon outside the first expansion cover and to expose the second balloon outside the second expansion cover.

22. The DCB catheter according to claim 19, wherein an inner diameter of the expanded second expansion cover is equal to or larger than a diameter of the pre-expanded second balloon.

23. The DCB catheter according to claim 13, wherein the outer surfaces of the first balloon and the second balloon are at least partially covered by a drug coating.

24. The DCB catheter according to claim 1, wherein the connecting member is selected from at least one of a hollow tubular structure, a filamentary structure, or a solid rod-shape structure.

* * * * *